(12) United States Patent
Al-Saadon

(10) Patent No.: US 9,486,342 B2
(45) Date of Patent: Nov. 8, 2016

(54) STENT SYSTEM, DEPLOYMENT APPARATUS AND METHOD FOR BIFURCATED LESION

(76) Inventor: Khalid Al-Saadon, Cornwall (CA)

( * ) Notice: Subject to any disclaimer, the term of this patent is extended or adjusted under 35 U.S.C. 154(b) by 92 days.

(21) Appl. No.: 14/239,611

(22) PCT Filed: Aug. 20, 2012

(86) PCT No.: PCT/CA2012/000771
§ 371 (c)(1),
(2), (4) Date: Feb. 24, 2014

(87) PCT Pub. No.: WO2013/026135
PCT Pub. Date: Feb. 28, 2013

(65) Prior Publication Data
US 2014/0214147 A1    Jul. 31, 2014

Related U.S. Application Data

(60) Provisional application No. 61/525,627, filed on Aug. 19, 2011.

(51) Int. Cl.
*A61F 2/954* (2013.01)
*A61F 2/856* (2013.01)
(Continued)

(52) U.S. Cl.
CPC .............. *A61F 2/954* (2013.01); *A61F 2/856* (2013.01); *A61F 2/958* (2013.01);
(Continued)

(58) Field of Classification Search
CPC .. A61F 2/954; A61F 2/958; A61F 2002/821; A61M 2025/1081
See application file for complete search history.

(56) References Cited

U.S. PATENT DOCUMENTS 4,994,071 A    2/1991  MacGregor
5,669,924 A *  9/1997  Shaknovich .............. A61F 2/07
                                              604/101.04
(Continued)

FOREIGN PATENT DOCUMENTS

WO    WO 9634580 A1    11/1996
WO    WO 9741803 A1    11/1997
WO    WO 2006033126 A1  3/2006

OTHER PUBLICATIONS

Feb. 2, 2015 EP Search Report for European Patent Application No. 12 825596.5.
(Continued)

*Primary Examiner* — Thomas McEvoy
(74) *Attorney, Agent, or Firm* — Kenneth F. Pearce

(57) ABSTRACT

A deployment apparatus and method for deploying one or more stents to a bifurcated vessel is provided. The invention is particularly suited for T-type bifurcated vessels where a side branch extends from a main branch. The deployment apparatus has a primary inflatable portion for engagement within the main branch and a secondary inflatable portion for engagement within the side branch. A main stent is arranged on the primary inflatable portion and radially expanded within the main branch while the secondary inflatable portion maintains registration with the side branch. A side branch stent is then arranged on the secondary inflatable portion and expanded within the side branch while the primary inflatable portion maintains registration with the expanded main stent. A bifurcated stent system suitable for bifurcated lesions is also provided comprising a side branch stent with a shaped end designed to engage a similarly shaped side opening in a main stent.

20 Claims, 10 Drawing Sheets

(51) Int. Cl.
*A61F 2/958* (2013.01)
*A61F 2/82* (2013.01)
*A61F 2/915* (2013.01)

(52) U.S. Cl.
CPC ... *A61F 2002/821* (2013.01); *A61F 2002/828* (2013.01); *A61F 2002/91558* (2013.01); *A61F 2250/0007* (2013.01)

(56) References Cited

U.S. PATENT DOCUMENTS

| | | | |
|---|---|---|---|
| 6,017,324 | A | 1/2000 | Tu et al. |
| 6,033,435 | A | 3/2000 | Penn et al. |
| 6,056,775 | A | 5/2000 | Borghi et al. |
| 6,210,429 | B1 | 4/2001 | Vardi et al. |
| 6,325,826 | B1 | 12/2001 | Vardi et al. |
| 6,740,113 | B2 | 5/2004 | Vrba |
| 7,481,834 | B2 | 1/2009 | Kaplan et al. |
| 2007/0208406 | A1* | 9/2007 | Alkhatib ............ A61F 2/958 623/1.11 |
| 2008/0033521 | A1* | 2/2008 | Jorgensen ......... A61F 2/958 623/1.11 |
| 2008/0125847 | A1* | 5/2008 | Krever ............... A61F 2/958 623/1.11 |
| 2011/0307047 | A1* | 12/2011 | Bourang ............ A61F 2/856 623/1.11 |

OTHER PUBLICATIONS

International Search Report for PCT CA/2012/000771 dated Sep. 11, 2012.
English Translation of the Jan. 5, 2016 SIPO Office Action for parallel Chinese Patent Application.

\* cited by examiner

STENT SYSTEM, DEPLOYMENT APPARATUS AND METHOD FOR BIFURCATED LESION

FIELD OF THE INVENTION

The present invention relates to a deployment apparatus and method for deploying one or more stents to a bifurcated vessel. The deployment apparatus is particularly suited for bifurcated vessels of the type comprising a main branch from which a side branch extends therefrom. The invention is also related to a bifurcated stent system suitable for use in bifurcated vessels.

BACKGROUND OF THE INVENTION

The term stent has been used interchangeably with terms such as intraluminal vascular graft and expansible prosthesis. As used throughout this specification, the term stent is intended to have a broad meaning and encompasses any expandable prosthetic device for implantation in a body passageway (e.g. a lumen or artery).

There have been various attempts at addressing the delivery and deployment of stents at bifurcated lesions. Bifurcated vessels may be of the Y-type, wherein a main branch bifurcates into two secondary branches, or of the T-type, wherein a side branch extends from a main branch. While the subject invention may be employed in certain circumstances with Y-type bifurcated vessels, it is primarily directed for use with T-type bifurcated vessels.

One common approach is to place a conventional stent in the main larger body lumen over the origin of the side branch. After removal of the stent delivery balloon, a second wire is introduced through a cell in the wall of the deployed stent and into the side branch. A balloon is then introduced into the side branch and inflated to enlarge that cell of the main vessel stent. A second stent is then introduced through the enlarged cell into the side branch and expanded therein.

Another strategy employed is the kissing balloon technique, in which separate balloons are positioned in the main and the side branch vessels and simultaneously inflated. Various two stent approaches including Culotte, T-stent and crush stent techniques have been employed as well as described in detail in U.S. Pat. No. 7,481,834 to Kaplan et al.

One of the drawbacks of the conventional stent techniques is that they run the risk of compromising the degree of the patency of the primary vessel and/or its branches or bifurcation. This may occur as a result of several problems, such as displacing disease tissue, vessel spasm, and dissection with or without intimal flaps, thrombosis, and embolism, that will increase the chance of restenosis.

These limitations have led others to develop specifically designed stents to treat bifurcation lesions. One approach employs a stent design with a side opening: U.S. Pat. Nos. 6,325,826 and 6,210,429 to Vardi et al.; U.S. Pat. No. 6,033,435 to Penn et al.; U.S. Pat. No. 6,056,775 to Borghi et al. A second approach includes a distal bifurcation of the stent: U.S. Pat. No. 4,994,071 to MacGregor; and U.S. Pat. No. 6,740,113 to Vrba. A third approach is having at least two axially aligned circumferential anchors: U.S. Pat. No. 7,481,834 to Kaplan et al.

Though these approaches have many theoretical advantages, they have shortcomings in:
 (a) Accurate positioning of the stent in the main vessel and the side branched or bifurcated lesion;
 (b) Adequate stent coverage which will result in high chance of restenosis;
 (c) Prevention of over-stretching of the proximal main artery when double balloons are used, as in the kissing balloon technique, which can damage the artery and increase the risk of restenosis in the stent.
 (d) Prevention of high metal to artery ratio resulted from crushing the struts of the main stent, in order to make an opening to access the side branch artery for deployment of the side branch stent, which increases fluid turbulence that may result in deposition of clot material which can cause blockage at the site of the bifurcation of the stent;
 (e) Prevention of the plaque shifting in the bifurcated arteries during balloon inflation;
 (f) In the case of the Kaplan et al. U.S. Pat. No. 7,481,834, insertion of traditional stent into a main vessel, after deployment of the new design stent in the side branched stent with anchor design, may pose a limitation to blood flow and access to the side branch vessel. The term 'stent jail' is often used to describe this concept.

Another drawback is with the balloon delivery system that assists in positioning the stent with accuracy in the bifurcated lesions, particularly involved in the procedure of double balloon sequential dilation for the stent, which has not proven to be very successful. These limitations have led others to develop specifically designed balloons to treat bifurcation lesions, such as in U.S. Pat. No. 6,017,324 to Tu et al. This design has its limitations in that it will help to solve specific bifurcation lesions when the distal branches have a Y-shape and the size of the distal vessels are smaller than the size of the proximal vessel (e.g. the aortic artery at bifurcation with iliac arteries) but it is not suitable if the size of one of the distal branches is equal to the proximal vessel size, and not suitable for the side branched vessels which are the majority of the cases.

Accordingly, there is a need for an improved stent design and delivery balloon apparatus and method of deployment, most particularly for application within the cardiac, coronary, renal, peripheral vascular, gastrointestinal, pulmonary, urinary and neurovascular system, and the brain, which:
 (1) Provides for a proper balloon stent delivery system and method for high accuracy for deployment of the stent in branched or bifurcated lesions;
 (2) Completely covers the bifurcation point of the bifurcation vessels with a high degree of accuracy;
 (3) Provides a proper balloon delivery system that will prevent overstretching of the proximal part of the main artery even where two balloons used as kissing balloons;
 (4) Prevents high metal to artery ratio at the bifurcation junction, by preventing crushing the struts of the main stent, in order to create an opening in the main stent to access the side branch artery;
 (5) Prevents the plaque shifting in the bifurcated arteries during balloon inflation;
 (6) Allows for differential sizing of the stents in bifurcated stent apparatus even after the main stent is implanted; and
 (7) Is usable to treat bifurcated vessels where the branch vessel extends from the side of the main vessel.

SUMMARY OF THE INVENTION

These and other disadvantages of the prior art are overcome by providing an inflatable deployment apparatus which has an inflatable side branch portion adapted to engage the side branch and maintain registration therewith. A method for deployment of one or more stents to a bifurcated vessel is also provided as is a stent system with a novel design that allows accurate placement thereof at the bifurcated junction.

In general, it is desirable to provide a branched balloon catheter, for performing balloon dilatation procedures in body lumen, particularly at bifurcated junctions. It is also desirable to provide a balloon catheter having branched portion adapted to engage a side branch of a bifurcated vessel. The "branched balloon" of this invention is also referred to as an inflatable apparatus having a main branch portion, with proximal and distal ends, wherein the branched portion originates from a mid-region the side of the main branch portion, preferably about mid-distance between the proximal and distal ends, and extends outwardly therefrom, preferable at an angle of between about 10 and 170° relative to the main branch portion.

The term "vessel" as used herein generally means a tubular tissue within the cardiac, coronary, renal, peripheral vascular, gastrointestinal, pulmonary, urinary and neurovascular systems and brain.

It is also desirable to provide a branched deployment apparatus balloon using over the wire means, wherein the wire means has a proximal end and two-head distal sections with two distal ends, one at the distal end of the main branch portion, and the second at the distal end at the branched portion. Alternately, the guide wire means may comprise two wires, each wire having its own distal end, and its own proximal end, wherein each wire is independently controllable.

It is also desirable to provide a method and a stented branched delivery catheter for treating stenosis or blocked vessels at the bifurcation region of the vascular vessel by precisely deploying the stent in place.

The inflatable "balloon" portions referred to herein are generally included within two broad classes. One class is considered non-compliant, and are formed from a generally non-stretchable material such as polyethylene, polyethylene terephthalate, polypropylene, cross-liked polyethylene, polyimide, and the like. The other class is considered compliant, formed from a generally compliant or stretchable material such as nylon, silicon, latex, polyurethane and the like.

While the inflatable portions can be unitary and contiguous, it would also be desirable to provide a deployment system which uses dual balloons, which are connectable to a common or separate supply of gas or fluid for inflation. By permitting inflation of the main branch portion and side branch portion with a single inflator/deflator device, identical inflation of both portions can be effected at the same time, which will reduce the shifting of the plaque inside the bifurcated coronary arteries.

The use of two balloons may provide for easier manufacture than a unitary and contiguous inflatable system, however, issues also arise with the use of two balloons as overlapping sections tend not to behave in the same manner upon expansion as non-overlapping sections. It would therefore be desirable to provide a restriction mechanism to moderate and control expansion of overlapping sections. Such a restriction mechanism may take the form of a sleeve which envelops the overlapping sections. The sleeve may assume a balloon like function which expands under inflation and collapses under deflation.

The invention described herein satisfies one or more of these desires. In particular, there is provided in accordance with one aspect of the invention an inflatable apparatus for deploying at least one stent in a bifurcated vessel having a main branch from which a side branch extends therefrom, comprising a primary inflatable portion having proximal and distal ends, and a secondary inflatable portion extending away from a region between the proximal and distal ends of the primary inflatable portion. The primary inflatable portion is positionable within the main branch and the secondary inflatable portion positionable within the side branch such that when the primary and secondary inflatable portions are inflated, the primary inflatable portion expands radially in the main branch while the secondary inflatable portion maintains registration with the side branch by expanding radially therein.

The primary and secondary inflatable portions may be contiguous. Alternately, the inflatable deployment apparatus may comprise a first balloon and a second balloon each having proximal and distal ends. A sleeve may be provided that surrounds the overlapping sections of the balloons. The distal end of the second balloon forms the secondary inflatable portion while the sleeve-surrounded proximal overlapping ends and the distal end of said first balloon form the primary inflatable portion. The sleeve is designed to restrict the expansion of the proximal overlapping ends of the balloons to the same extent as the expansion of the distal end of the first balloon so as to provide a relatively uniform expansion of the so-called main branch portion.

According to another aspect of the invention, there is provided a method for deployment of at least one stent in a bifurcated vessel having a main branch from which a side branch extends therefrom, comprising:
providing an inflatable apparatus having a primary inflatable portion and a secondary inflatable portion;
arranging a first stent on the primary inflatable portion;
deploying the inflatable apparatus to the site of the bifurcated vessel and positioning the primary inflatable in the main branch and the secondary inflatable portion in the side branch;
inflating the primary and secondary inflatable portions so as to cause the first stent to radially expand within the main branch while the secondary inflatable portion maintains registration with the side branch.

The method may further comprise positioning the secondary inflatable portion through an opening in the first stent when arranging the first stent on the primary inflatable portion.

The method may further comprise removing the inflatable apparatus once the first stent has been expanded;
arranging a second stent on the secondary inflatable portion;
redeploying the inflatable apparatus by positioning the primary inflation portion within the expanded first stent and positioning the secondary inflatable apparatus in the side branch;
inflating the primary and secondary inflatable portions so as to cause the second stent to expand radially within the side branch while the primary inflatable portion maintains registration with the main branch.

The second stent may further comprise alignment means for orienting the proximal end of said second stent with the opening of said first stent.

According to a further aspect of the invention, there is provided a stent system for a bifurcated vessel having a main branch from which a side branch extends therefrom, comprising:
a first radially expandable stent for supporting the walls of the main branch; and a second radially expandable stent for supporting the walls of the side branch;

the second stent having a shaped proximal end;

the first stent having an opening in a side wall thereof, the opening having a shape which engages with the shaped proximal end of the second stent upon expansion.

The second stent may further comprise alignment means for orienting the proximal end of the second stent with the opening of the first stent.

The alignment means may comprise an expandable alignment brace extending from the proximal end of the second stent. The alignment brace is positionable though the opening in the first stent and expandable within the internal circumference of the first stent so as to align the shaped end of the second stent with the opening of the first stent. The alignment brace when expanded may provide additional support to the first stent at or about its opening.

The opening of the first stent may be shaped to complement the shaped end of the second stent upon expansion. In this regard, the shape of the opening of the first stent and the shaped end of the second stent may be based on the geometries of intersecting cylinders. The length and diameter of the stents may be selected based on the predetermined shapes of the main and side branches. The first and second stents may intersect at a relative angle of between about 10° and 170°.

The stent apparatus of the invention offers significant and novel advantages over prior art stents in that the stents of the invention (1) permit precise deployment of the main stent and branched stent in the bifurcated lesions; (2) provide better coverage for the bifurcated lesions; (3) accommodate different sizing for the main and branched stents, thus providing better fit; and (4) may be used to treat only the main vessel of the bifurcation lesion, while preserving complete access to the other branch without 'stent jail' of the side branch.

The invention may therefore be used as a double-stent apparatus and a single-stent apparatus, each of which may be used to cover the origin of the bifurcation in a branched vessel. As a single-stent apparatus, the invention may be used to treat only one branch of the bifurcation while leaving access to the second branch unobstructed. The invention may be used to provide different sizes and lengths of the branched balloon delivery system and different sizes and lengths of the stents needed to be delivered in the bifurcated lesions.

The stent apparatus of the present invention is image-able by methods commonly used during catheterization such as x-ray or ultra-sounds.

These objects and other object advantages and features of the invention will become better understood from the detailed description of the invention and the accompanying drawings.

DETAILED DESCRIPTION OF THE INVENTION

Figure 1:
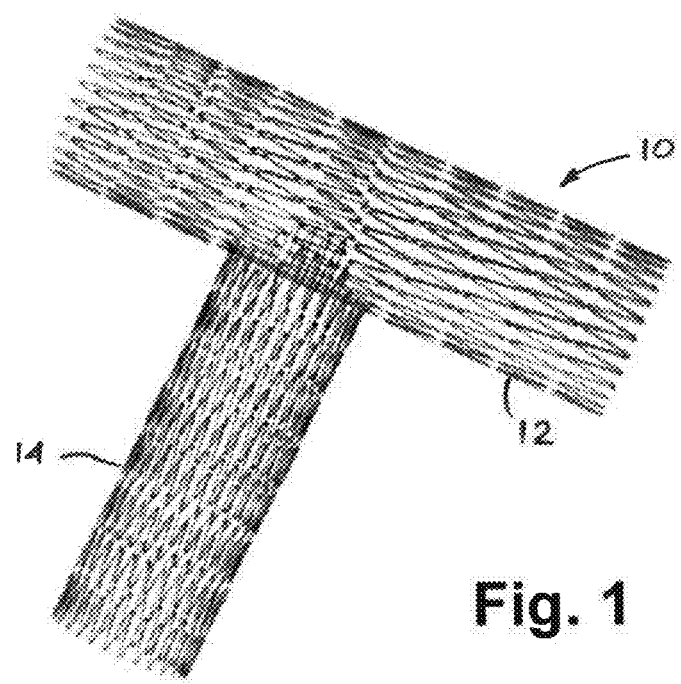
FIG. 1 illustrates a perspective view a branched stent in its expanded state, according to one embodiment of the invention.
Figure 2:
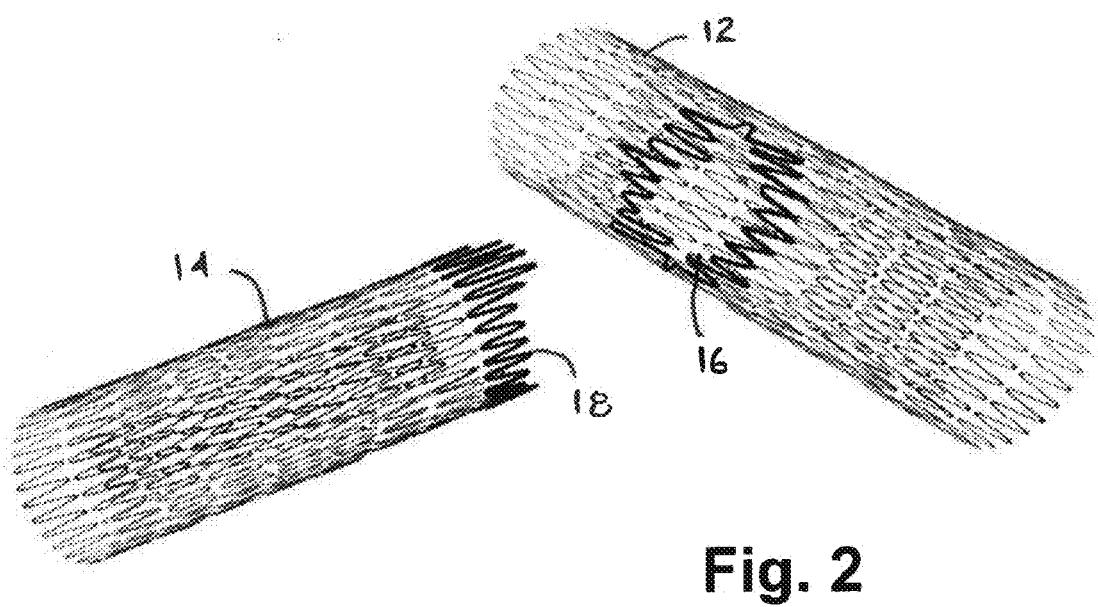
FIG. 2 is an exploded perspective view of the branched stent, with the engagement elements highlighted.
Figure 3:
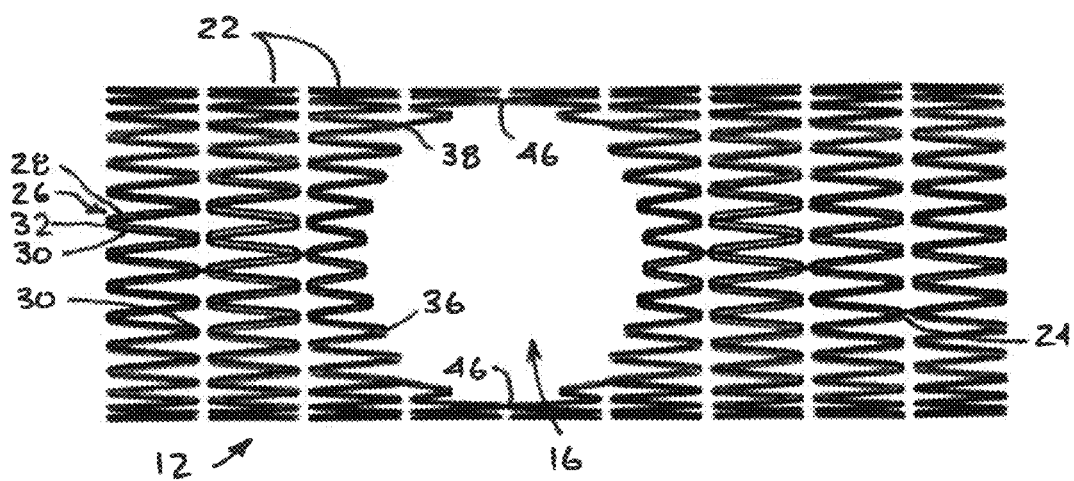
FIG. 3 is an elevational view of the main branch stent with the back portion removed for clarity.
Figure 4A:
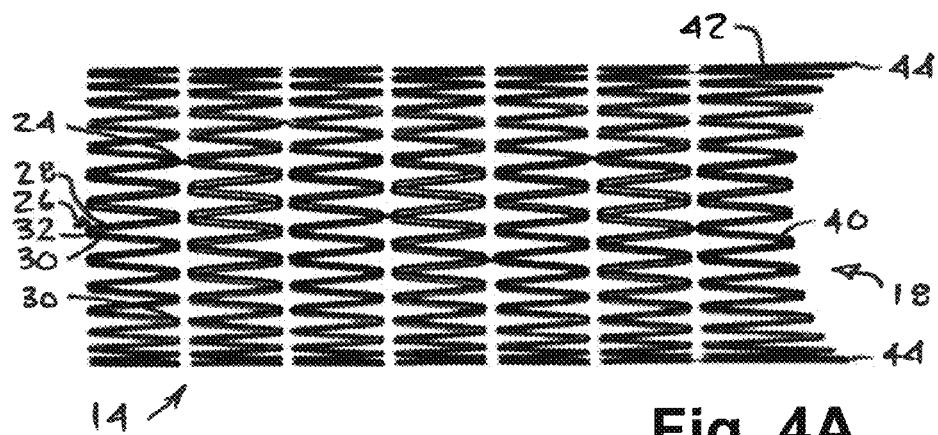
FIG. 4A is a side elevational view of the side branch stent according to one embodiment.
Figure 4B:
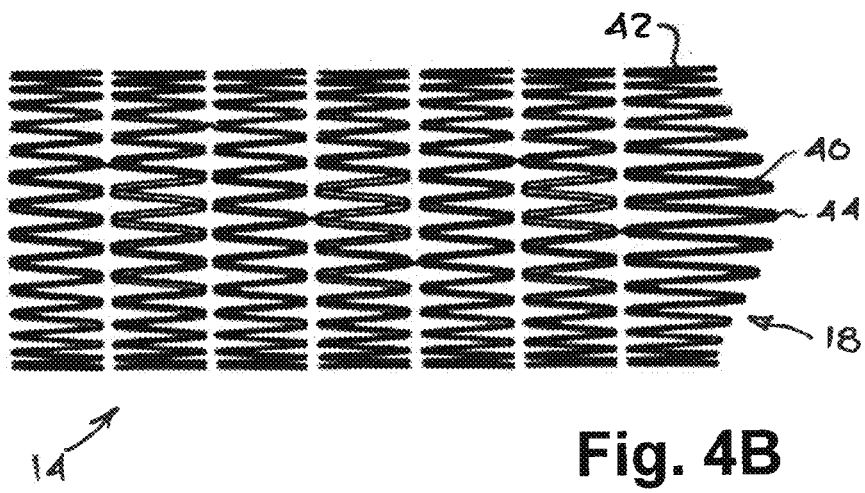
FIG. 4B is a top view of the side branch stent shown in FIG. 4A.

With reference to FIGS. 1 and 2, an embodiment of a bifurcated stent system 10 according to the invention is illustrated. The bifurcated stent system 10 comprises a generally tubular main stent 12 and a generally tubular side branch stent 14. The main stent 12 is provided with a side opening 16 in its cylindrical wall matrix adapted to engage and mate with the proximal end 18 of the side branch stent 14. In general, when expanded, the side branch stent 14 has an end shape which complements the opening 16 in the main stent 12, which minimizes the over-entanglement of stent wires when the stents have been cooperatively expanded, thereby minimizing the potential of obstruction of blood flow at or near the juncture. The opening 16 may be circular, elliptical, diamond-shaped or may closely approximate the intersection of two cylinders at various geometries. Although the side branch stent 14 is shown in FIG. 1 as extending approximately 90° from the main stent 12, the stents 12,14 may be designed in various shapes and sizes and with various geometries to approximate or match the geometry of the bifurcation of the vessels to be treated. For example, the side branch stent 14 shown in FIGS. 4A and 4B are of a slightly smaller diameter than the main branch stent 12 shown in FIG. 3.

The stents 12,14 are made using conventional materials and technology. As shown in FIGS. 3, 4A and 4B, the stents 12,14 may comprise a plurality of adjacent rings 22 which are longitudinally joined by connectors 24 disposed at selective spaces between adjacent rings 22. Rings 22 generally comprise a plurality of functional units 26 consisting of a pair of arms 28,30 connected by a deformable or bendable joint 32. In the unexpanded state, the arms 28,30 of stents 12,14 are generally parallel to the longitudinal axes of stents 12,14. The stents 12,14 are flexible substantially along their longitudinal axes when in their unexpanded or constricted state and are relatively more rigid along their longitudinal axes when expanded. When the stents 12,14 are expanded, joints 32 deform to allow the arms 28,30 to angularly displace and to thereby allow rings 22 to circumferentially expand in a serpentine manner.

An opening 16 is provided in the side of main stent 12 which is adapted to be engaged by the shaped end 18 of side branch stent 14 when expanded. In this regard, the functional units 36 about the opening 16 may be of differing lengths and may be connected differently such as at 38 to ensure the opening 16 forms into the appropriate shape when the main stent 12 is expanded and/or to provide additional support at the opening 16. Likewise, the functional units 40 of the end ring 42 that forms the shaped end 18 of side branch stent 14 may be of varying lengths to ensure the shaped end 18 forms into the appropriate complementary shape when the side branch stent 14 is expanded. As shown in FIGS. 4A and 4B, the end ring 42 has functional units 44 that extend farthest at the top and bottom (in the orientation shown in FIG. 4A) that engage the parts of the opening 46 which are relatively farther away at the top and bottom (in the orientation shown in FIG. 3).

Figure 5:
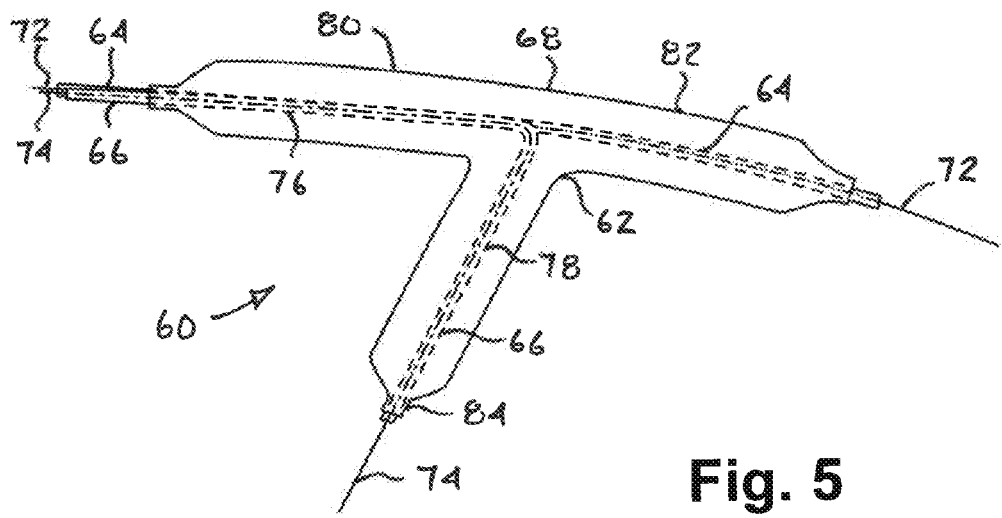
FIG. 5 is a schematic representation of a side branched balloon apparatus according to one embodiment of the invention.

FIG. 5 illustrates an embodiment of the inflatable apparatus 60, also known as a balloon dilatation catheter (shown in its inflated state) for deploying one or more stents to a birfurcated vessel region according to one embodiment of the invention. The balloon dilatation catheter 60 comprises a bifurcated balloon 62 and a pair of catheter lumens 64,66. The bifurcated balloon 62 comprises a main balloon portion 68 and a branch balloon portion 70. Catheter lumens 64,66 are provided to allow the balloon dilatation catheter 60 to be deployed to the bifurcated vessel region through the use of guide wires 72,74. Specifically, lumen 64 runs through the proximal portion 80 and distal portion 82 of main balloon portion 68 and accommodates the main branch guide wire 72. Lumen 66 accommodates the side branch guide wire 74. The proximal portion 76 of lumen 66 runs through the proximal portion 80 of main balloon 68 and through the entire branch balloon portion 70, exiting at the distal end 84 of branch balloon portion 70. When the terms proximal and distal are used herein, they normally imply relativity to the insertion of the catheter.

Catheter lumens 64,66 also provide the means by which the interior of the inflatable portions communicate with the supply of gas or fluid for inflation. The supply can be a single source or separate sources may be provided, which can be controlled unitarily or separately.

Although two separate lumens 64,66 have been shown, it is envisaged that a single lumen extending through the balloon catheter may be provided with a common lumen section in the proximal main balloon portion which bifurcates into a first distal lumen section in the distal portion of the main balloon and a second distal lumen section in the branch balloon section. It will be understood by those skilled in the art that the guide wires may be part of a rapid exchange wire system or and over the wire exchange system.

Figure 6:
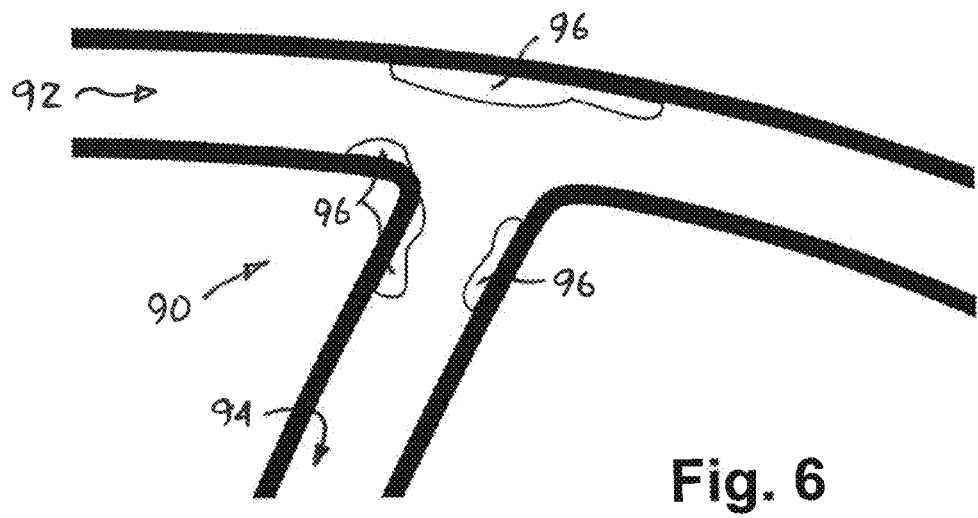
FIG. 6 is a schematic representation of a bifurcated vessel and in particular a side branched bifurcated vessel.

FIG. 6 shows a typical bifurcated vessel 90 of the T-type comprising a main vessel 92 and a side branch vessel 94 extending therefrom and having plaque or lesions 96 at or about the juncture 98 of the vessels 92,94.

Figure 7:
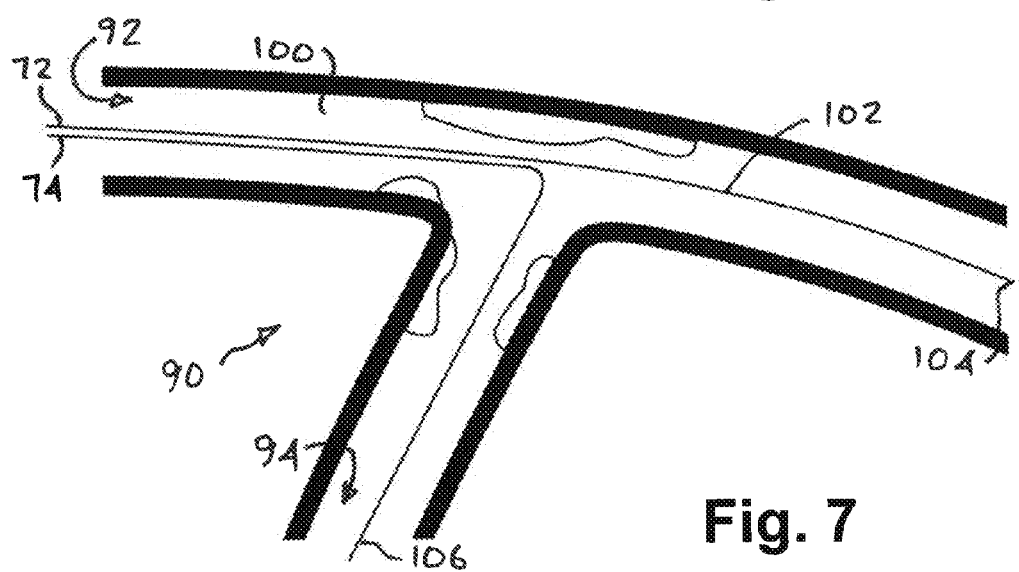
FIGS. 7-16 are schematic representations illustrating the manner in which the inflatable balloon apparatus and stent system according to one aspect of the invention is deployed in a side branched bifurcated vessel.

FIGS. 7-16 will be used to illustrate the methodology of accurate placement of the stent system 10 in the bifurcated vessel 90 using the inflatable deployment apparatus 60 according to one aspect of the invention. As shown in FIG. 7, guide wires 72,74 are inserted through the proximal portion 100 of main vessel 92. The distal end 104 of main guide wire 72 is positioned in the distal portion 102 of the main vessel 92 while the distal end 106 of the branch guide wire 74 is positioned in the side branch vessel 94.

Figure 8:
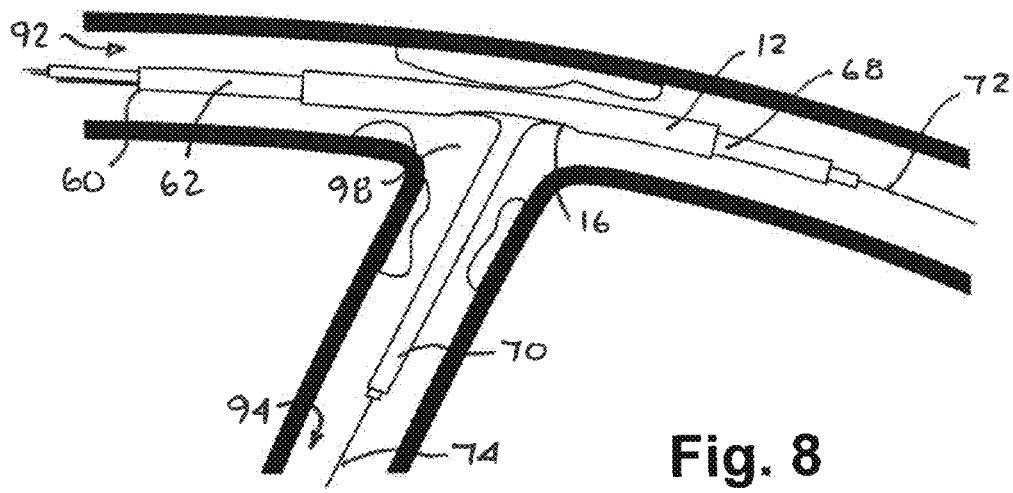

As shown in FIG. 8, the inflatable deployment apparatus 60 having the main stent 12 positioned over the main balloon portion 70 is inserted into the vessel 90 with the bifurcated balloon 62 in a collapsed, unexpanded state. For ease of illustration, the stents 12,14 are shown schematically without their wire matrix structure. The structure of the stents 12,14 is such that in their collapsed, unexpanded state, they are relatively flexible along their longitudinal axes, allowing them to be delivered through the relatively tortuous paths that comprise the body's veins and arteries. However, when expanded, stents 12,14 become significantly rigid and inflexible, allowing them to provide substantial circumferential support to the vessel walls. The side branch balloon 70 extends through the side opening 16 in the main stent 12 and is positioned in the side branch vessel 94. By sliding the bifurcated balloon 62 in the collapsed state over the placed guide wires 72,74, with the main stent 12 over the main balloon 68, the main stent 12 will be positioned accurately in the main vessel 92, with side opening 16 of the main stent 10 is positioned accurately at the juncture 98 of the side branch vessel 94 on account of the registration of the side branch balloon 70 within branch vessel 94.

Figure 9:
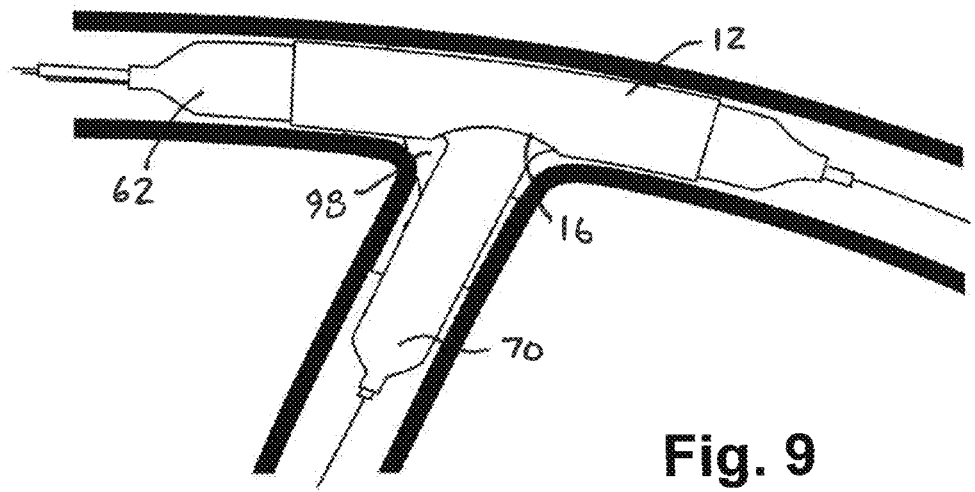
Figure 10:
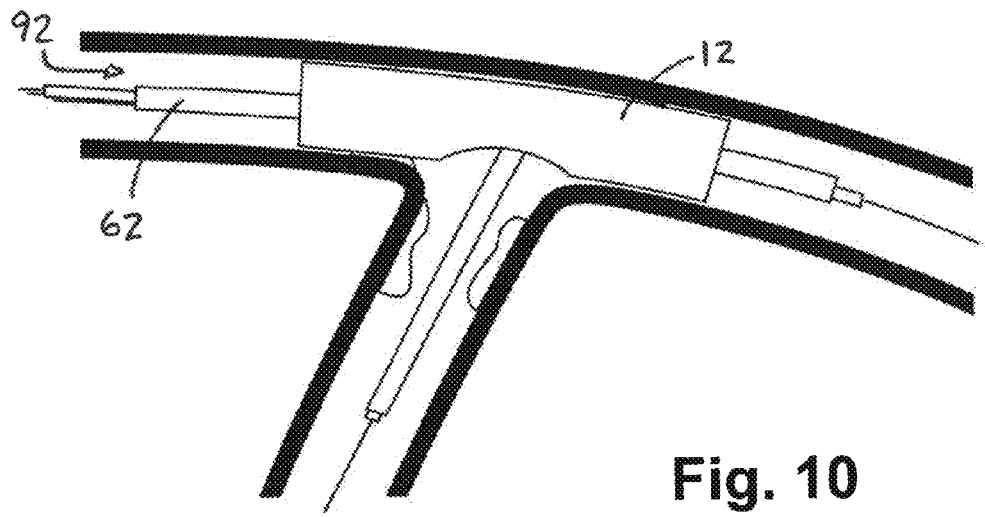
Figure 11:
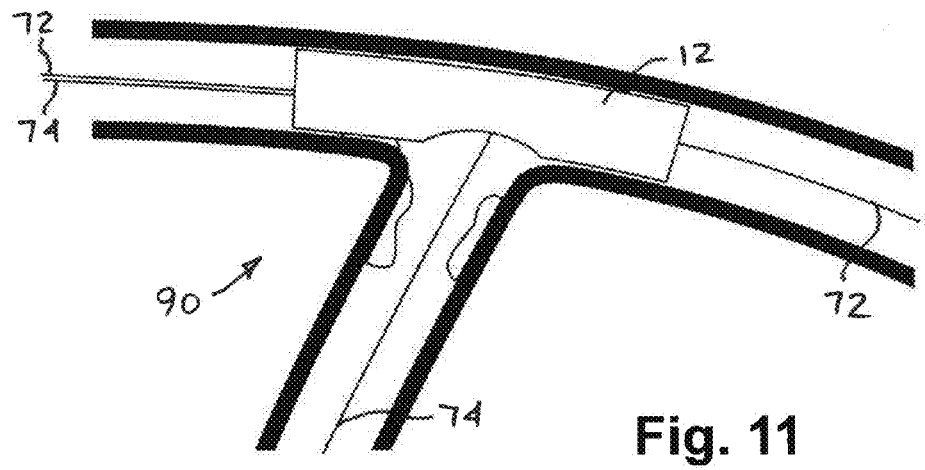

As shown in FIG. 9, the bifurcated balloon 62 is expanded, causing main stent 12 to circumferentially expand. The side opening 16 maintains good registration with the juncture 98 of the side branch vessel 94 due to the expansion of the side branch balloon portion 70. The bifurcated balloon 62 is then deflated as shown in FIG. 10, leaving the main stent 12 in accurate position within the main vessel 92. The inflatable deployment apparatus 60 with deflated bifurcated balloon 62 is then withdrawn from the bifurcated vessel 90 leaving the guide wires 72,74 in place as shown in FIG. 11.

Figure 12:
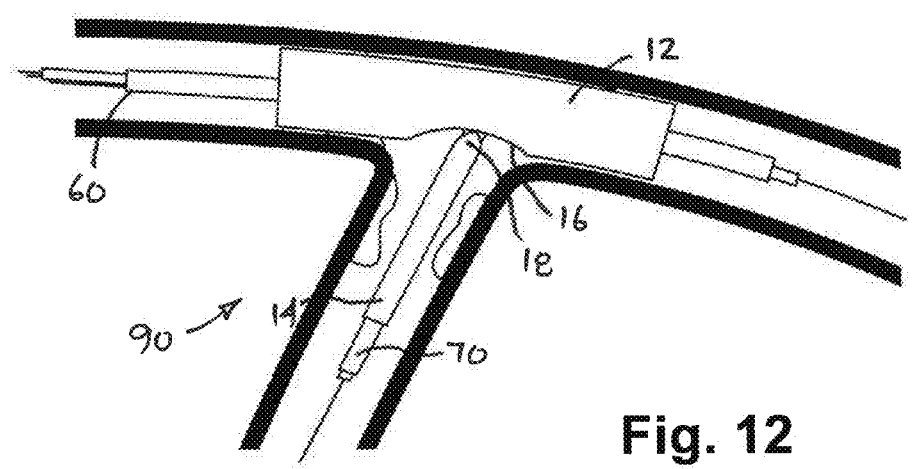
Figure 13:
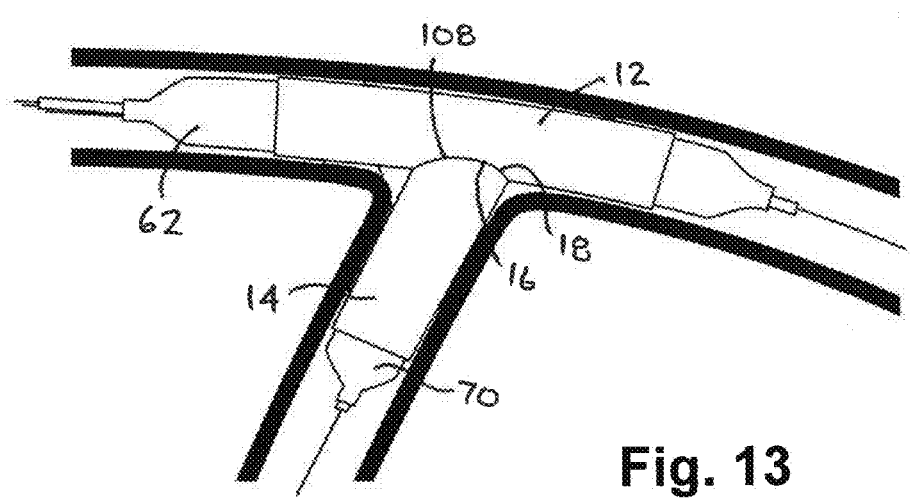

In reference to FIG. 12, there is illustrated the deployment of the side branch stent 14, which has been arranged on the side branch balloon portion 70 of a bifurcated balloon 62, with the side branch stent 14 positioned such that its shaped end 18 will be in appropriate alignment with the opening 16 of the main stent 12 when expanded. The inflatable deployment apparatus 60 is repositioned using guide wires 72,74 into the bifurcated vessel 90 as explained previously. The bifurcated balloon 62 is then inflated as shown in FIG. 13, thereby causing side branch stent 14 to circumferentially expand about inflating side branch balloon portion 70. As the stents 12,14 are precisely positioned, the end 18 of the side branch stent 14 engages precisely within the opening 16 of the main stent 12 at the junction 98, forming a relatively clean, minimally intrusive, intersection 108 therebetween due to the complementary shapes.

Figure 14:
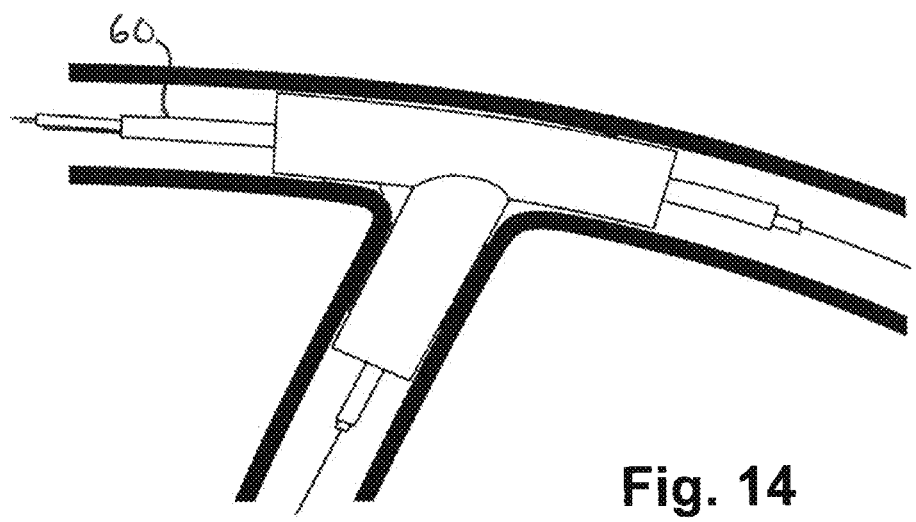
Figure 15:
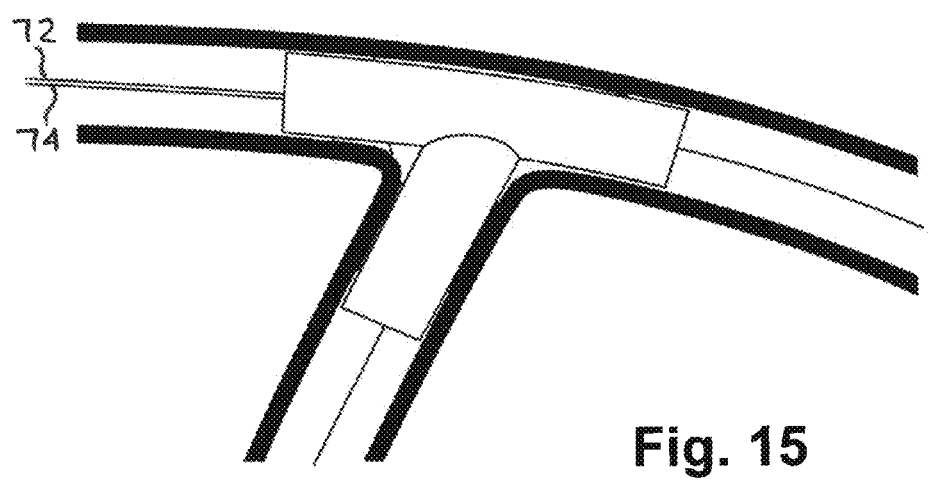
Figure 16:
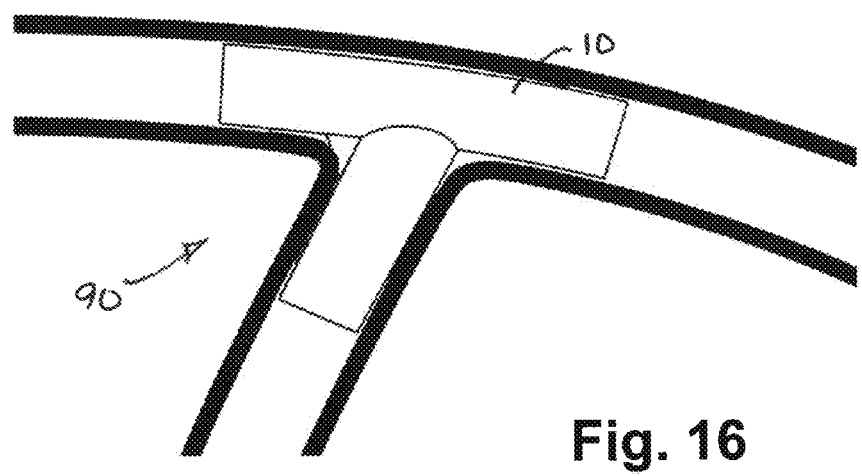

The bifurcated balloon 62 is then deflated as shown in FIG. 14 and the inflatable deployment apparatus 60 withdrawn as shown in FIG. 15. The guide wires 72,74 are then withdrawn as shown in FIG. 16, leaving the bifurcated stent system 10 accurately placed in the bifurcated vessel 90.

Figure 17A:
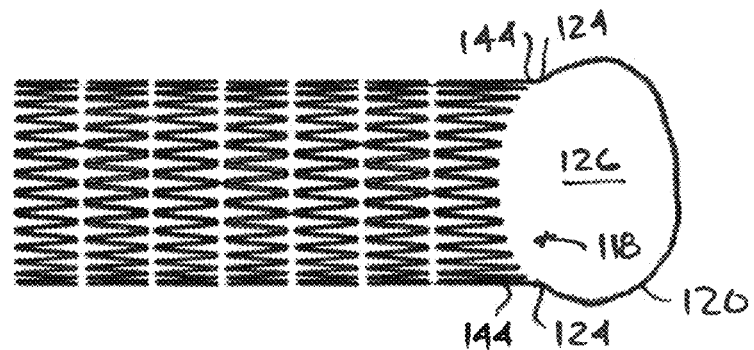
FIG. 17A is a side elevational view of an alternate side branch stent accordingly to an alternate embodiment of the stent system.
Figure 17B:
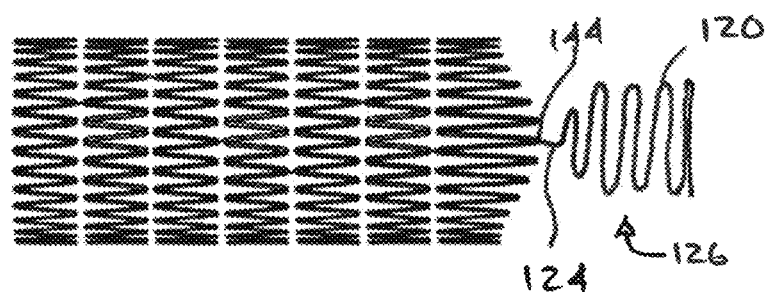
FIG. 17B is a top view of the alternate side branch stent shown in FIG. 17A.

An alternate embodiment of the bifurcated stent system is shown in FIGS. 17A and 17B. More particularly, the alternate bifurcated stent system comprises a modified branch stent 114, similar to branch stent 14, but having an alignment brace 120 extending from the shaped proximal end 118. The alignment brace 120 is generally semicircular in the transverse direction (transverse to the longitudinal axis of the branch stent) as shown in FIG. 17A. The modified branch stent 114 is designed to pair with a main branch stent 112 (not shown in FIGS. 17A-B) which is generally identical with the main stent 12 of the stent system 10. The purpose of the alignment brace 120 is to permit more assured alignment of the modified branch stent 114 with the main branch stent 112, and more particularly, more accurate positioning of the shaped end 118 of the modified branch stent 114 with the complementary opening 116 of the main branch stent 112, as will be seen in FIGS. 18-20.

The alignment brace 120 is attached to the extended functional units 144 of the shaped end 118 at deformable joints 124 to thereby form a generally tubular transverse opening 126 which, when expanded, is adapted to approximate the internal circumference of the main stent.

Figure 18:
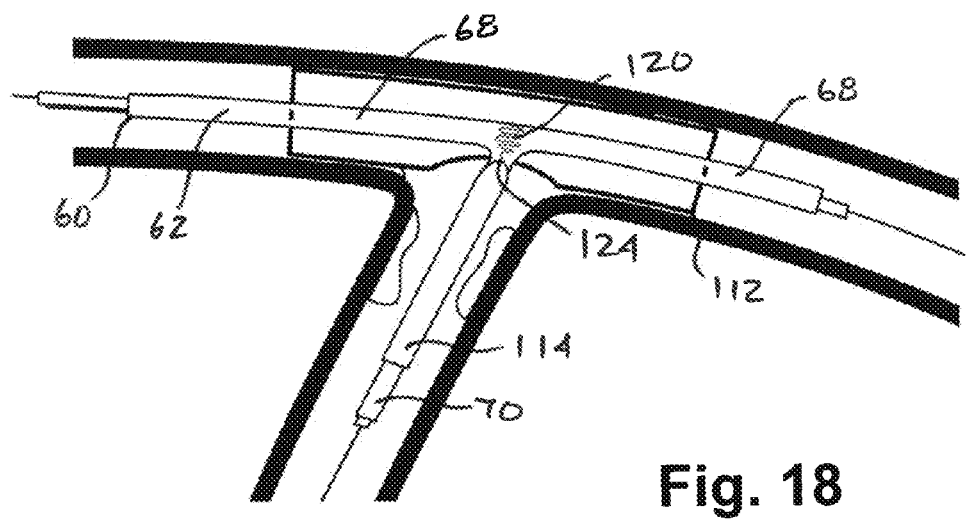
FIGS. 18-20 are schematic representations illustrating the manner in which the inflatable balloon apparatus and alternate stent system is deployed in a side branched bifurcated vessel.
Figure 19:
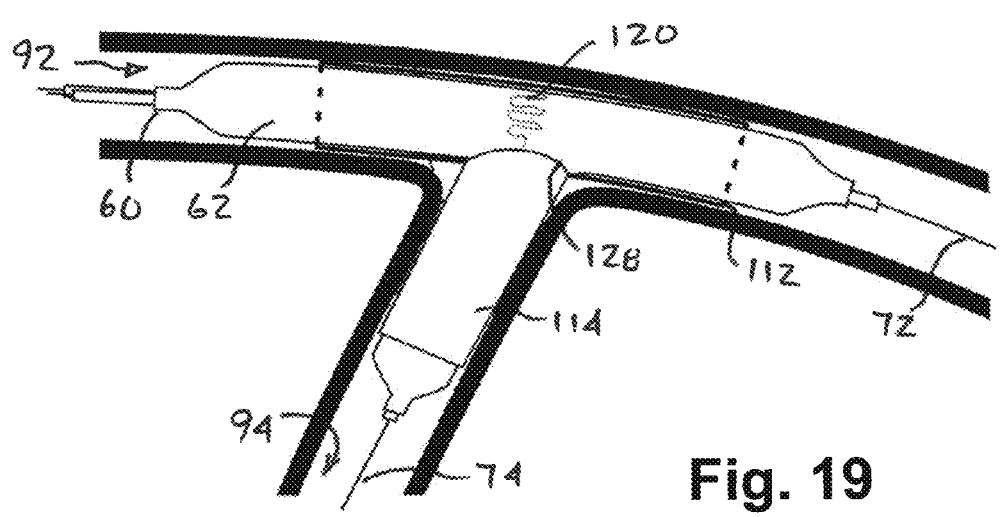
Figure 20:
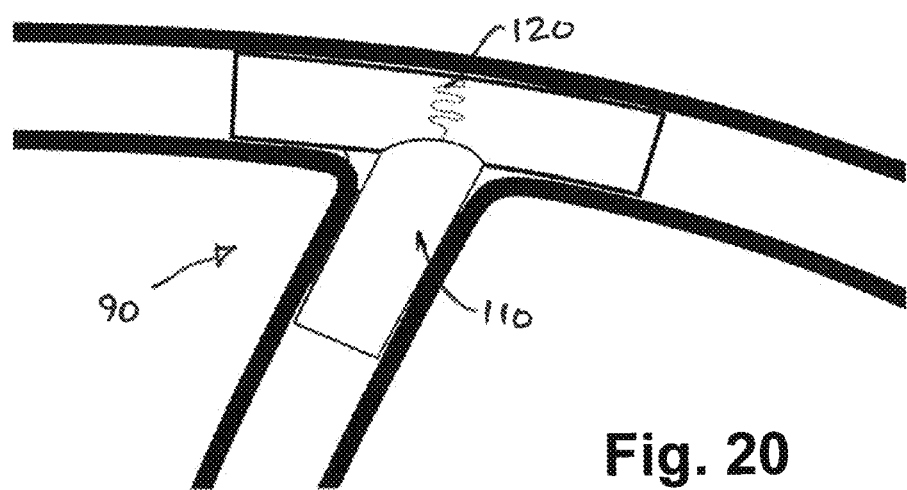

FIGS. 18-20 show, in part, the methodology of accurate placement of the alternate stent system 110 in a bifurcated vessel 90 according to an alternate aspect of the invention using the inflatable deployment apparatus 60. FIG. 18 shows the main stent 112 already deployed in the bifurcated vessel 90. The deployment of the main stent 112 is the same as the deployment of main stent 12 described above in connection with FIGS. 6-11. The main stent 112 is shown schematically in cross-section in FIGS. 18-20 (i.e. only the rear half showing) to better illustrate the operation of the alignment brace 120.

In reference to FIG. 18, there is illustrated the deployment of the modified side branch stent 114, which has been arranged on the side branch balloon portion 70 of the bifurcated balloon 62, with the main branch balloon portion 68 positioned though the alignment brace 120. As mentioned above, the alignment brace 120 is attached to the side branch stent 114 by deformable joints 124. This allows the alignment brace 120 to bend relative to the longitudinal axis of the side branch stent 114 so as to permit the side branch balloon portion 70 to be parallel with the main balloon portion 68 for insertion purposes and to permit bending back into alignment with the longitudinal axis of the side branch stent 114 when the inflatable deployment apparatus 60 reaches the bifurcation with branch balloon 70 extending into the side branch 94 as shown in FIG. 18. The arrangement of the alignment brace 120 over the main balloon 68 permits highly accurate positioning of the side branch stent 114 so as to guarantee that the shaped end 118 will align precisely with the opening 116 in the main stent 114. In this regard, as shown in FIG. 19, the bifurcated balloon 62 is inflated, causing the side branch stent 114 to circumferentially expand in the branch vessel 94 about the branch balloon 70 and to simultaneously expand alignment brace 120 about the expanding main balloon 68 within the main stent 112. The expanding alignment brace 120 maintains the orientation of the shaped end 118 with the expanding opening 116 of the main stent to better ensure accurate engagement therebetween upon full expansion. The alignment brace 120 also minimizes the potential for gaps or overlap which can occur at the intersection 128 when there is no such means for maintaining the registration of the opening 116 and end shape 118 of the stents 112,114. A better intersection with potentially less gaps or overlaps therebetween will promote better dynamic fluid flow and thereby reduce fluid turbulence, which will result in a reduction in the possibility of stenosis of the stent by blood products.

The expanded alignment brace 120 also provides additional bracing support of the internal wall of main stent 114, particularly around the area of the opening 116 where the main stent 114 will be least rigid.

The bifurcated balloon 60 is then deflated and withdrawn along with the guide wires 72,74 as shown in FIG. 20, leaving the modified bifurcated stent system 110 accurately placed in the bifurcated vessel 90.

Figure 21:
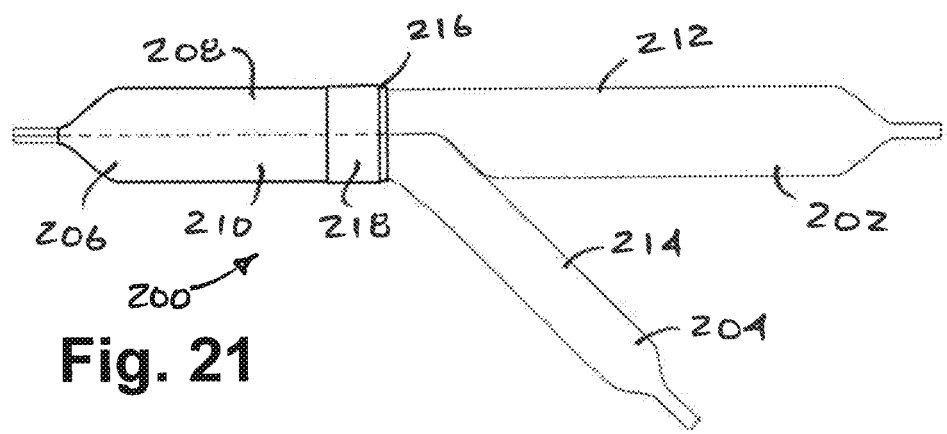
FIG. 21 is a schematic representation of an alternate deployment apparatus comprising dual balloons which extend from a sleeve.

Besides constructing the inflatable balloon apparatus with a unitary inflatable balloon as shown in FIG. 5, it is also possible to construct it with using a pair of balloons. The difficulty in using two balloons at a T-shaped bifurcated vessel is the balloons have to overlap in one side of the main branch. When expanded, this causes the overlapping balloon portions to expand more than the portion of the balloon in the other side of the main branch, resulting in uneven circumferential expansion of the stent in the main branch. To overcome this problem, a restrictive member, such as a sleeve, may be positioned around the portions of the balloons which overlap. In this regard, there is shown in FIG. 21 an alternative embodiment to the unitary inflatable balloon 62. A dual balloon deployment apparatus 200 comprises a first balloon 202 and a second balloon 204 which are encased in a sleeve 206 at their proximal ends 208,210 which overlap. The balloons 202,204 may be supplied with an inflatable gas or liquid from a common source so as to be inflatable and deflatable in unison. The sleeve 202 is designed to restrict the expansion of the proximal ends 208,210 of balloons 202,204 to the same extent as the expansion of the distal end 212 of the first balloon 202. The distal end 214 of the second balloon 204 extends from the sleeve opening 216 at a region between the proximal and distal ends 208,212 of the first balloon. The main branch and side branch stents (not shown) are disposed on the deployment apparatus 200 in the same manner as the inflatable apparatus 60, with the main stent spanning the sleeved proximal ends 208,210 of the first and second balloons 202,204 and the distal end 212 of the first balloon 202, and with the distal end 214 of the second balloon 204 extending through the opening of the main stent. In this manner, the main stent may be expanded uniformly as the first and second balloons 202,204 are expanded.

In construction of the dual balloon deployment apparatus 200, using the sleeve 206, an adhesive process or technology is required, to assure the bonding of the fabrics materials from which the balloons 202,204 are made. In this embodiment, lamination processes were used to secure the attachment of all materials to each other. After lamination is achieved, the balloon sleeve 206 and the first and second balloons 202,204 will behave as one unit. In this regard, the sleeve 206 will expand and collapse, upon the inflation and deflation of the balloons 202,204.

To provide additional support at the sleeve opening 216, an optional support band 218 may be provided to prevent the sleeve 210 from tearing upon inflation. The support band 200 may be attached to the sleeve 210 by a lamination process to secure the bonding of the fabrics materials.

Figure 22:
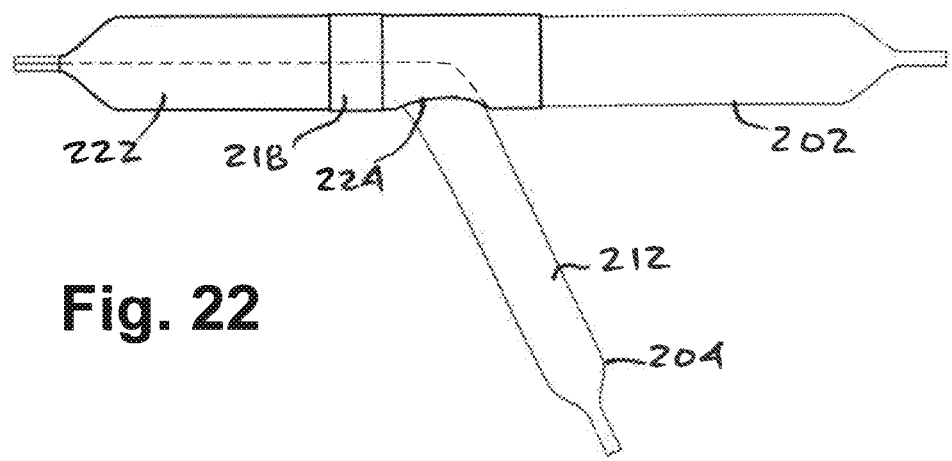
FIG. 22 shows the alternate deployment apparatus of FIG. 22 with a modified sleeve.

To provide better angular support for the distal end 212 of the second (side branch) balloon 204, a longer sleeve 222 as shown in FIG. 22 may be provided which includes an opening 224 through which the distal end 212 of the second balloon 204 exits. The longer sleeve 222 may also be provided with the optional sleeve 218 for greater support near the proximal side of opening 224.

Figure 23:
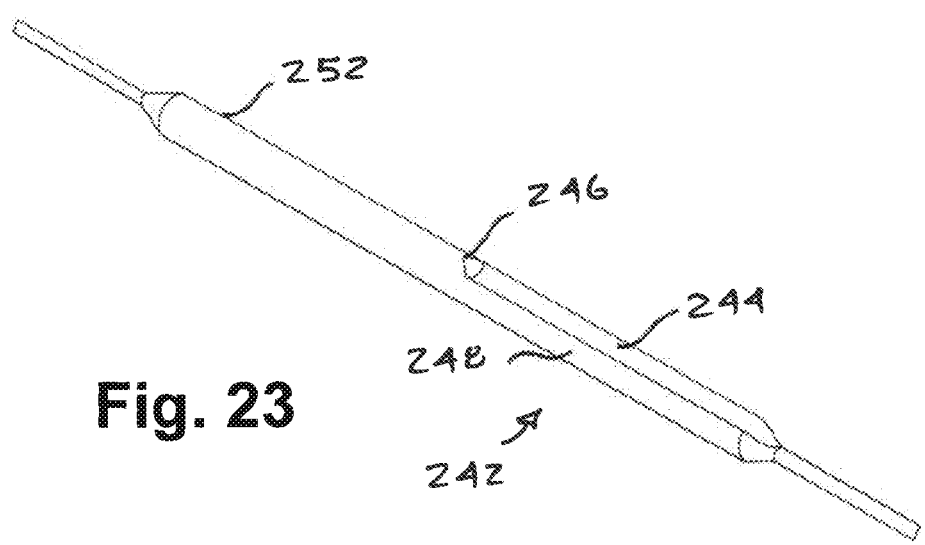
FIG. 23 is a perspective view illustrating an alternate embodiment of the first balloon of a dual balloon deployment apparatus.

An alternate embodiment of the first balloon in its expanded state is shown at 242 in FIG. 23 in which there is provided a longitudinal groove 242 that extends along the proximal end portion 248 to about the midpoint or a point 246 between the proximal end 248 and distal end 252 where the distal end of the second balloon (not shown in FIG. 23) is adapted to extend. The groove 244 helps reduce any over-expansion of the proximal ends of the balloons within the sleeve and, hence, over-stretching of the vessel walls during expansion.

Figure 24:
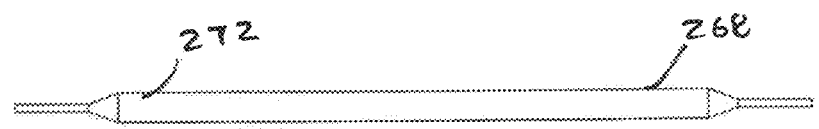
FIGS. 24 to 27 are side views illustrating various alternate embodiments of the second balloon of a dual balloon deployment apparatus.
Figure 25:
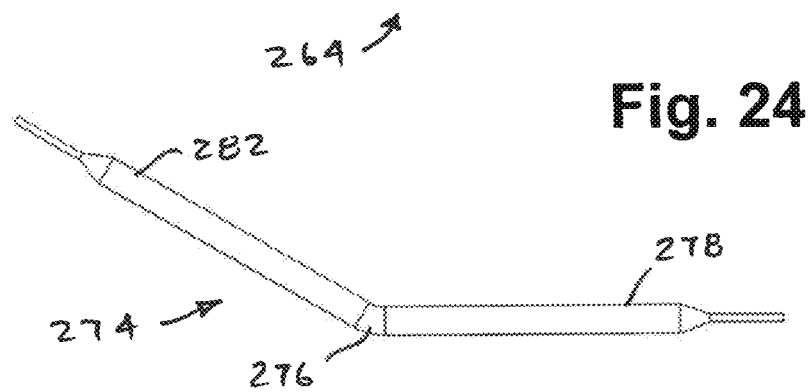
Figure 26:
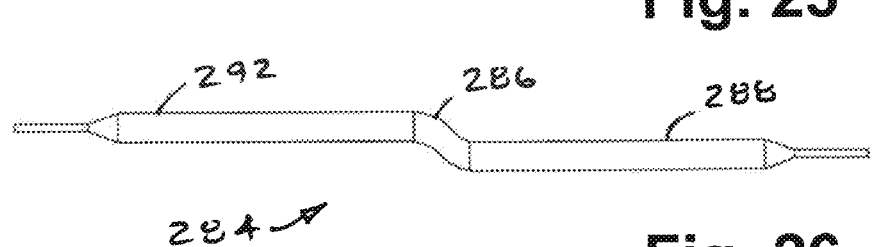

Embodiments of the second balloon are shown in FIGS. 24 to 27. FIG. 24 shows a second balloon 264 as having a uniform tubular shape with substantially equal-sized proximal 268 and distal 272 ends. To help ease the stress at the bending point, another embodiment of the second balloon 274 is formed with an angular bend 276, as shown in FIG. 25, between the proximal 278 and distal 282 ends. The reduction in stress may also lessen the propensity of tearing of the sleeve during inflation. In FIG. 26, there is shown at 284 an alternate embodiment of the second balloon of FIG. 25, wherein a reverse bend 286 is provided between the proximal 288 and distal 292 ends. The reverse bend 286 allows the distal end 292 of the second balloon 284 to remain substantially parallel to the first balloon (not shown) for ease of insertion.

Figure 27:
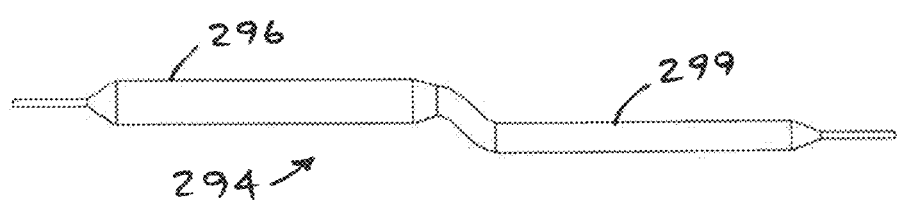

Another modification in the shape of the side branch second balloon of FIG. 26 is shown in FIG. 27. In this embodiment, the second balloon 294 is provided with a proximal end 298 which is of reduced diameter relative to the diameter of the distal end portion 296. Again the advantage of reducing the diameter size of the proximal 298 portion of the side branch second balloon 294 is that it will help reduce stress on the sleeve, as well as the possible over-expansion of the stent and the associated overstretching of the vessel during the full inflation of both balloons inside the balloon sleeve.

Figure 28:
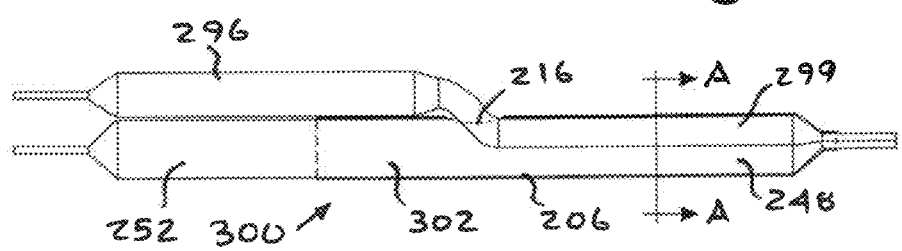
FIG. 28 is a side view of a preferred embodiment of the dual balloon deployment apparatus.
Figure 29:
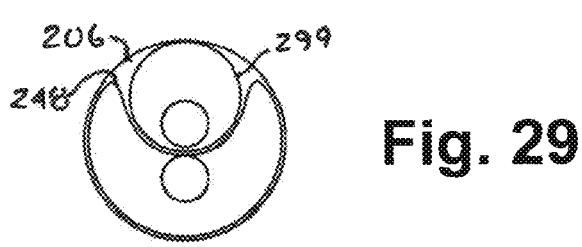
FIG. 29 is a cross-sectional view taken along lines A-A of FIG. 28 showing the internal details of the proximal portion of the preferred dual balloon deployment apparatus.

In FIG. 28, there is shown a preferred embodiment of a dual balloon deployment apparatus 300 comprising the grooved first balloon embodiment 242 as shown in FIG. 23 with the second balloon embodiment 294 as shown in FIG. 26, and sleeve 222 as shown in FIG. 22. The reduced diameter proximal end portion 298 of the second balloon 294 seats within groove 244 in the proximal end portion 248 of the first balloon 242 as can be best seen in cross-section in FIG. 29. Sleeve 222 surrounds the proximal end portions 248,298 of the first and second balloons 242,294 and extends along a section 302 of the distal end portion 252 of the first balloon 242. The distal end portion 296 of the second balloon 294 extends through the sleeve opening 216. The proximal end portions 248,298 of the first and second balloons 242,294 and the distal end portion 252 of the first balloon 242 forms a primary inflatable portion for expanding the main stent in the main vessel while the distal end portion 296 of the second balloon 294 maintains registration with the side branch vessel and may subsequently be used to expand a side branch stent into the side branch vessel.

Although there have been shown various embodiments and examples of the inflatable deployment apparatuses, the bifurcated stent systems and methods of deploying stents at bifurcated lesions, it will be appreciated by those skilled in the art that these embodiments and examples should not be considered limiting and that various modifications and substitutions may be made to the inventions defined in the appended claims without departing from the spirit and scope of the invention.

The invention claimed is:

1. A stent system and an inflatable apparatus for deploying the stent system in a bifurcated vessel having a main branch from which a side branch extends therefrom, said inflatable apparatus comprising:
 a primary inflatable portion having proximal and distal ends, and a secondary inflatable portion extending away from a region between said proximal and distal ends of said primary inflatable portion; said primary inflatable portion positionable within said main branch and said secondary inflatable portion positionable within said side branch such that when said primary and secondary inflatable portions are inflated, said primary inflatable portion expands radially in said main branch while said secondary inflatable portion maintains registration with said side branch by expanding radially therein;
 said stent system comprising:
 a first radially-expandable stent positionable on said primary inflatable portion, wherein when said primary inflatable portion is inflated, said first stent radially expands within said main branch, said first radially-expandable stent comprising a side opening through which said secondary inflatable portion extends; and
 a second radially-expandable stent positionable on said secondary inflatable portion, wherein when said secondary inflatable portion is inflated, said second stent radially expands, said second stent having a proximal and distal end and said proximal end being shaped to complement a shape of said opening of said first stent upon expansion;
 said second stent further comprising an expandable alignment brace extending from said proximal end of said second stent and positionable within said opening of said first stent for orienting a shaped proximal end of said second stent with said opening of said first stent and for maintaining registration of said shaped end and said opening upon expansion, said alignment brace being adapted to have said primary inflatable portion extend therethrough, so that when said primary and secondary inflatable portions are inflated, said primary inflatable portion expands said alignment brace within an internal circumference of said first stent and aligns said second stent's shaped end with said opening of said first stent.

2. The system and apparatus of claim 1, wherein said expandable alignment brace when expanded provides additional support to said first stent at or about said first stent's opening.

3. The system and apparatus of claim 1, wherein said alignment brace is attached to said shaped end by deformable joints and forms a generally tubular transverse opening upon expansion.

4. The system and apparatus of claim 1, wherein a diameter to which said secondary inflatable portion is inflatable is less than a diameter to which said primary inflatable portion is inflatable.

5. The system and apparatus of claim 1, wherein length of said primary inflatable portion is different than length of said secondary inflatable portion.

6. The system and apparatus of claim 1, wherein shapes of said inflatable portions are selected on predetermined shapes of said main and said side branches.

7. The system and apparatus of claim 1, wherein said primary and secondary inflatable portions are inflatable concurrently.

8. The system and apparatus claim 1, wherein said primary and secondary inflatable portions are inflatable separately.

9. The apparatus of claim 1, wherein said inflatable portions are contiguous.

10. The system and apparatus of claim 1 further comprising first and second lumens, said first lumen for a main branch guide wire and said second lumen for a side branch guide wire.

11. The system and apparatus of claim 1, comprising:
a first balloon and a second balloon, each having proximal and distal ends;
a sleeve surrounding said proximal ends of said balloons;
a distal end of said second balloon forming said secondary inflatable portion;
sleeve-surrounded proximal ends of said balloons and a distal end of said first balloon forming said primary inflatable portion.

12. The system and apparatus of claim 11, wherein said secondary inflatable portion extends from a distal end of said sleeve.

13. The system and apparatus of claim 11, wherein said secondary inflatable portion extends through a side aperture provided in said sleeve.

14. The system and apparatus of claim 13 further comprising a support band encircling said sleeve and positioned at or near a proximal end of said side aperture.

15. The system and apparatus of claim 11, wherein said sleeve restricts expansion of said proximal ends of said first and second balloons to substantially the same extent as expansion of said distal end of said first balloon extending from an end of said sleeve.

16. The system and apparatus of claim 15, wherein said second balloon includes a bend section to angle said distal end away from said primary inflatable portion.

17. The system and apparatus of claim 16, wherein said second balloon includes a reverse bend section to allow said distal end to remain parallel to said primary inflatable portion for ease of insertion.

18. The system and apparatus of claim 11 further comprising a support band encircling said sleeve and positioned about where said proximal ends of said balloons emerge.

19. The system and apparatus of claim 11, wherein said first balloon includes a groove in its proximal end portion which longitudinally accommodates a portion of said proximal end of said second balloon.

20. The system and apparatus of claim 1, wherein said secondary balloon portion extends at an angle of between 10° and 170°.

* * * * *